United States Patent [19]
Ludwig

[11] Patent Number: 5,919,677
[45] Date of Patent: Jul. 6, 1999

[54] EUKARYOTIC AND RETROVIRAL ANTISENSE INITIATOR ELEMENTS

[75] Inventor: Linda B. Ludwig, East Aurora, N.Y.

[73] Assignee: The Research Foundation of State University of New York, Amherst, N.Y.

[21] Appl. No.: 08/853,703

[22] Filed: May 9, 1997

[51] Int. Cl.⁶ .............................. C07H 21/04; C12N 5/16; C12N 15/11; C12P 19/34
[52] U.S. Cl. .................. 435/172.3; 435/91.2; 435/320.1; 435/325; 435/375; 536/24.1; 536/24.5; 536/25.3
[58] Field of Search .............................. 435/6, 7.21, 91.2, 435/172.1, 172.3, 320.1, 325, 375, 419; 514/44; 536/24.1, 24.5, 25.3; 935/33, 34, 35, 36, 37, 22, 24

[56] References Cited

PUBLICATIONS

Gielow et al. Expression of the replication protein Arp of phasyl shows dual regulation by an antisense promoter. EMBO J. 10(10): 3061–3066, 1991.

Lefranc et al. gd lineage specific transcription of human T cell receptor g genes by a combination of a non–lineage–specfic enhancer and silencers. Eur. Immunol. 25: 617–622, 1995.

Malik et al. Identification of an antisense WT1 promoter in intron 1: implications for WT1 gene regulation. Oncogene 11: 1589–1595, 1995.

Spicer et al. An antisense promoter of the murine c–myc gene is localized within intron 2. Mol. Cell. Biol. 12(3): 1324–1329, Mar. 1992.

Sawada et al. A lineage–specific transcriptional silencer regulates CD4 gene expression during T lymphocyte development. Cell 77: 917–929, Jun. 1994.

Winoto et al. ab lineage specific expression of the a T cell receptor gene by nearby silencers. Cell 59: 649–655, Nov. 1989.

Michael et al., "Negative Strand RNA Transcripts are Produced in HIV–1–Infected Cells and Patients by a Novel Promoter Downregulated by Tat", J. Virology, vol. 68, pp. 979–987, 1994.

Miller, "Human Immunodeficiency Virus May Encode a Novel Protein on Genomic DNA Plus Strand", Science, vol. 239, pp. 1420–1422, 1988.

*Primary Examiner*—Nancy Degen
*Assistant Examiner*—Thomas G. Larson
*Attorney, Agent, or Firm*—Hodgson, Russ, Andrews, Woods & Goodyear, LLP

[57] ABSTRACT

Identified are genetic regulatory elements which are part of a natural antisense RNA negative regulatory system in eukaryotic cells. The genetic regulatory elements, designated an antisense initiator sequence, when downstream of and operably linked to a DNA molecule can transcribe the DNA molecule into RNA transcripts of negative strand polarity that function to bind to, in forming an RNA duplex with, sense RNA transcripts being produced from a target gene to be regulated. The invention relates to recombinant vectors useful for introduction into eukaryotic cells, and methods of using the vectors to regulate expression of a target gene comprising introducing the recombinant vectors into host eukaryotic cells.

29 Claims, 8 Drawing Sheets

5,919,677

SEQUENCE LISTING (1) GENERAL INFORMATION:

(iii) NUMBER OF SEQUENCES: 9

(2) INFORMATION FOR SEQ ID NO:1 :

(i) SEQUENCE CHARACTERISTICS:
      (A) LENGTH: 7 nucleotides
      (B) TYPE: nucleic acid
      (C) STRANDEDNESS: double-stranded
      (D) TOPOLOGY: linear (ii) MOLECULE TYPE: DNA (iii) HYPOTHETICAL: No (iv) FEATURE:
      (A) OTHER INFORMATION: /note "R" = A or G, "W" = A or T,
         and "N" = A, T, C, or G (v) SEQUENCE DESCRIPTION: SEQ ID NO:1 :

RRWNTGR       7

(2) INFORMATION FOR SEQ ID NO:2 :

(i) SEQUENCE CHARACTERISTICS:
        (A) LENGTH: 8 nucleotides
        (B) TYPE: nucleic acid
        (C) STRANDEDNESS: double-stranded
        (D) TOPOLOGY: linear (ii) MOLECULE TYPE: DNA (iii) HYPOTHETICAL: No (iv) SEQUENCE DESCRIPTION: SEQ ID NO:2 :

```
GATCTGAG                                                              8
```

(2) INFORMATION FOR SEQ ID NO:3 :

(i) SEQUENCE CHARACTERISTICS:
        (A) LENGTH: 98 nucleotides
        (B) TYPE: nucleic acid
        (C) STRANDEDNESS: double-stranded
        (D) TOPOLOGY: linear (ii) MOLECULE TYPE: DNA (iii) HYPOTHETICAL: No (iv) SEQUENCE DESCRIPTION: SEQ ID NO:3 :

```
GGGTCTCTCT GGTTAGACCA GATCTGAGCC TGGGAGCTCT CTGGCTAACT               50

AGGGAACCCA CTGCTTAAGC CTCAATAACC CTATAGTGAG TCGTATTA                 98
```

(2) INFORMATION FOR SEQ ID NO:4 :

(i) SEQUENCE CHARACTERISTICS:
        (A) LENGTH: 63 nucleotides
        (B) TYPE: nucleic acid
        (C) STRANDEDNESS: double-stranded
        (D) TOPOLOGY: linear (ii) MOLECULE TYPE: DNA (iii) HYPOTHETICAL: No (iv) SEQUENCE DESCRIPTION: SEQ ID NO:4 :

```
CTGCTTTTTG CCTGTACTGG GTCTCTCTGG TTAGACCAGA TCTCCCTATA               50

GTGAGTCGTA TTA                                                       63
```

(2) INFORMATION FOR SEQ ID NO:5 :

(i) SEQUENCE CHARACTERISTICS:
        (A) LENGTH: 8 nucleotides
        (B) TYPE: nucleic acid
        (C) STRANDEDNESS: double-stranded
        (D) TOPOLOGY: linear (ii) MOLECULE TYPE: DNA (iii) HYPOTHETICAL: No (iv) SEQUENCE DESCRIPTION: SEQ ID NO:5 :

```
AGAGTGGG                                                              8
```

(2) INFORMATION FOR SEQ ID NO:6 :

(i) SEQUENCE CHARACTERISTICS:
        (A) LENGTH: 7 nucleotides
        (B) TYPE: nucleic acid
        (C) STRANDEDNESS: double-stranded (D) TOPOLOGY: linear (ii) MOLECULE TYPE: DNA (iii) HYPOTHETICAL: No (iv) SEQUENCE DESCRIPTION: SEQ ID NO:6 :

AATATGG                                                              7

(2) INFORMATION FOR SEQ ID NO:7 :

(i) SEQUENCE CHARACTERISTICS:
            (A) LENGTH: 8 nucleotides
            (B) TYPE: nucleic acid
            (C) STRANDEDNESS: double-stranded
            (D) TOPOLOGY: linear (ii) MOLECULE TYPE: DNA (iii) HYPOTHETICAL: No (iv) SEQUENCE DESCRIPTION: SEQ ID NO:7 :

AGTCTGGG                                                             8

(2) INFORMATION FOR SEQ ID NO:8 :

(i) SEQUENCE CHARACTERISTICS:
            (A) LENGTH: 153 nucleotides
            (B) TYPE: nucleic acid
            (C) STRANDEDNESS: double-stranded
            (D) TOPOLOGY: linear (ii) MOLECULE TYPE: DNA (iii) HYPOTHETICAL: No (iv) FEATURE: HIV aINR comprises nucleotides 96 to 103

(v) SEQUENCE DESCRIPTION: SEQ ID NO:8 :

GGCGTGGCCT GGGCGGGACT GGGGAGTGGC GAGCCCTCAG ATGCTGCATA                50

TAAGCAGCTG CTTTTTGCCT GTACTGGGTC TCTCTGGTTA GACCAGATCT                100

GAGCCTGGGA GCTCTCTGGC TAACTAGGGA ACCCACTGCT TAAGCCTCAA                150

TAA                                                                  153

(2) INFORMATION FOR SEQ ID NO:9 :

(i) SEQUENCE CHARACTERISTICS:
            (A) LENGTH: 25 nucleotides
            (B) TYPE: nucleic acid
            (C) STRANDEDNESS: single-stranded
            (D) TOPOLOGY: linear (ii) MOLECULE TYPE: DNA (iii) HYPOTHETICAL: No (iv) SEQUENCE DESCRIPTION: SEQ ID NO:9 :

CCAGAGAGAC CCAGTACAGG CAAAA                                          25

EUKARYOTIC AND RETROVIRAL ANTISENSE INITIATOR ELEMENTS

This invention was made, in part, with government support under grant numbers R29AI38114 and R01MH47225 awarded by the National Institutes of Health. The government has certain rights in this invention.

BACKGROUND OF THE INVENTION

1. Field of the Invention

The present invention relates to regulation of gene expression in eukaryotic cells. More particularly, the invention relates to a novel and natural antisense RNA negative regulatory system utilizing a genetic element which provides a mechanism by which antisense transcripts are generated.

2. Description of the Background and Related Art

The general mechanism by which transcription of eukaryotic genes is initiated typically involves interaction between several factors including promoters (including initiator elements), enhancers, DNA-binding proteins, and a transcriptional complex comprising an RNA polymerase and associated transcription factors. Typically, an AT-rich region, the TATA motif, is positioned upstream from the start of transcription and is necessary for many promoters to initiate transcription by an RNA polymerase efficiently and accurately. In promoters with or without a TATA box, initiator elements can serve to orient the transcription factors for RNA polymerase II. However, the rate of initiation of transcription is determined by one or more DNA-binding proteins that recognize promoter/enhancer elements in the proximity of the initiation of transcription complexes. Presumably, a DNA-binding protein can influence either the initiation of transcription complexes or the propensity of the complexes to elongate once initiated.

The 5' long terminal repeat (LTR) of the human immunodeficiency virus (HIV) is a prototypic enhancer-promoter unit containing a standard TATA box, an initiation site (Rittner et al., 1995, *J. Mol. Biol.* 248:562–580), and upstream elements (e.g., Sp1 and NF-κB) that are commonly found in many viral and cellular genes, and which are influenced by viral and cellular DNA-binding proteins (see, e.g., review by Jones, 1989, *New Biologist* 1:127–135). From the HIV double-stranded intermediate, and from the HIV promoter located in the 5' LTR, mRNAs of plus strand polarity are transcribed from minus strand (also called "template") DNA (see Definitions section herein). Depending on the transcript, the MRNA may then be translated into one or more viral proteins including Gag, Pol, Vif, Tat, Vpu, Vpr, Rev, Env, and Nef.

Effective transcription from the HIV promoter is dependent on the presence of Tat for transcriptional activation that dramatically increases the levels of viral mRNAs. In the absence of Tat, predominately short mRNA transcripts are transcribed from the minus strand DNA. These short transcripts terminate near a cis-acting element, the transactivation-responsive region (TAR; Selby et al., 1989, *Genes Dev.* 3:547–558). Also in the absence of Tat, transcribed is a low basal level of viral mRNAs. Tat function is mediated through TAR, located downstream from the initiation site for transcription. The TAR region, present on a transcript, folds in an energetically favored RNA secondary structure or RNA-stem loop structure (see FIG. 1) which acts as a binding site for Tat. It has been demonstrated that in the absence of Tat, the majority of polymerases that have initiated transcription prematurely disengage from the template. Upon binding of TAR by Tat, Tat acts independently of other promoter elements to stimulate elongation (Rittner et al., 1995, supra). Initiator elements (INRs) have been reported to be necessary for efficient initiation of transcription in mammalian cells in the absence of a TATA box (Javahery et al., 1994, *Mol. Cell Biol.* 14:116–127; Smale and Baltimore, 1989, *Cell* 57:103–113). There is uncertainty as to why basal (Tat-independent) transcription from the HIV LTR in vivo is relatively low, and whether there is some repression mechanism affecting the HIV 5' LTR.

A possibility was raised that the plus strand of the viral DNA contains a long open reading frame (ORF), located in the region of the genome complementary to the env gene sequence, that may encode a viral protein (Miller, 1988, *Science* 239:1420–1422). However, it is not apparent whether this possibility was confirmed, such as by the demonstration of the putative protein or its respective mRNA. The possibility that bidirectional transcription occurs in HIV was further evaluated by Michael et al. (1994, *J. Virol.* 979–87). It was discovered that a weak negative strand promoter in the U3 region of the 3'LTR of HIV is responsible for the production of RNA transcripts of negative strand polarity. What role (if any) such RNA transcripts, produced from the weak negative strand promoter in the 3' LTR, have in the HIV life cycle remains to be elucidated.

Pathways by which viral or cellular gene expression are regulated (whether involving transcription and/or translation) are targets for intervention. More particularly, the regulation of production of recombinant proteins for industrial or medical applications is a common goal of the biotechnology industry. Using HIV as an example, the transactivation functions have been used to develop HIV-specific and sensitive bioassays (Felber and Pavlakis, 1988, *Science* 239:184–7), and to evaluate the effects of drugs on the ability of HIV to infect and replicate (see, e.g., Schwartz et al., 1989, *Proc. Natl. Acad. Sci. USA* 86:7200–7203). Several approaches have been attempted for the antisense inhibition of cellular or viral gene expression. For example, antisense inhibition of HIV replication has met with variable degrees of success in inhibiting some function of the virus. Sites in HIV that are targeted for antisense inhibition include the LTR, the U5 region, the U3 region, the R region, the primer binding site region, the AUG start codon region, the polyP region, RNA splice sites, the leader region, the tat splice site, the rev splice site, and the cap site (see, e.g. U.S. Pat. No. 5,580,761 to Greatbatch et al.). It has also been suggested that synthesized oligonucleotides antisense to the TAR stem-loop may be capable of disrupting the secondary structure of the TAR stem-loop (Vickers et al., 1991, *Nucleic Acids Res.* 19:3359–3368; U.S. Pat. No. 5,512,438 to Eckers), or antisense to tat MRNA (U.S. Pat. No. 5,166,195 to Ecker), thereby ultimately disrupting transactivation mediated by the binding of Tat to TAR.

Accordingly, there has been and continues to be a long-felt need for the intracellular production of antisense molecules which are capable of effectively functioning to regulate gene expression at either a transcriptional and/or translational level. Desirably, such an approach to antisense therapy would employ, and thereby "turn up" a mechanism of control of transcription and/or translation that may be found intrinsically in mammalian cells.

SUMMARY OF THE INVENTION

The present invention relates to the discovery of a natural and novel mechanism endogenous to eukaryotic cells for modulating gene expression at the transcriptional and/or translational level. The mechanism disclosed is a natural antisense RNA regulatory system, with a key component of the system comprising an antisense initiator sequence (aINR). The aINR orients RNA polymerase II enabling generation of one or more antisense transcripts; i.e., initiates production of RNA transcripts of negative strand polarity utilizing the plus strand DNA as a template. It has now been discovered that the aINR initiates production of natural antisense RNA transcripts that function to bind to, in forming a duplex with, complementary sense RNA transcripts. The resultant bidirectional transcription, and the formation of such RNA duplexes, modulates gene expression by inhibiting transcription to sense mRNA transcripts. One mechanism of modulation of gene expression mediated by RNA duplex formation is destabilization of the RNA polymerase thereby potentiating premature termination of sense mRNA transcripts. Thus, this mechanism may result in the inhibition of transcriptional elongation or cause short (less than full length) mRNA or RNA sense transcripts to be transcribed from the minus strand DNA.

While noting that the aINR is double-stranded, the 7 base consensus sequence (5' to 3') of the aINR is G/A G/A A/T N T G G/A, wherein the first nucleotide can be G or A; the second nucleotide can be G or A; the third nucleotide can be A or T; the fourth nucleotide can be G, A, T or C; the fifth nucleotide can be T; the sixth nucleotide can be G; and the seventh nucleotide can be G or A. In a further embodiment of the present invention, the aINR may comprise an additional nucleotide on the 3' end, an eighth nucleotide, comprising a G or an A.

In accordance with the present invention, compositions and methods of modulating gene expression are provided. A vector is constructed which contains at least one copy of an aINR down stream of at least one copy of a nucleic acid molecule (coding strand of a target gene). Downstream of the aINR may be placed some regulatory elements (e.g., CAAT box in either orientation; or TATA box, in reverse orientation with respect to the consensus sequence of the aINR). The resultant recombinant vector is then introduced into cells expressing the target gene to be modulated. Once in the cells, from the recombinant vector the aINR initiates production of antisense RNA transcripts by RNA polymerase II. The antisense RNA transcripts then modulate the expression of the target gene by forming RNA duplexes with the sense MRNA being transcribed from the target gene. Since transcription of the target gene is inhibited, there are few, if any, full-length sense mRNA transcripts available to be translated into the protein encoded by the target gene. Therefore, such modulation may result in a decrease in the amount of such protein produced by the treated cells.

DETAILED DESCRIPTION OF THE INVENTION

Definitions

Figure 1:
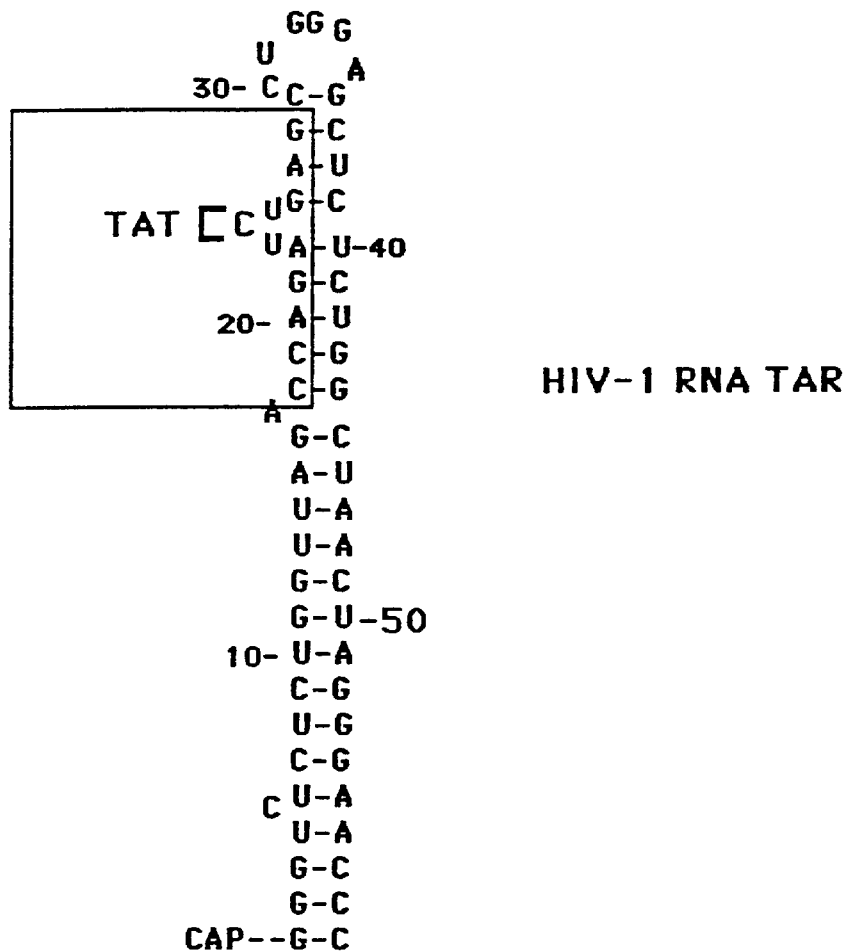
FIG. 1 is a schematic representation of the HIV-1 TAR and adjacent region which shows the location of an HIV-1 antisense initiator sequence (aINR) (SEQ ID NO:2) designated by the arrow.
Figure 2A:
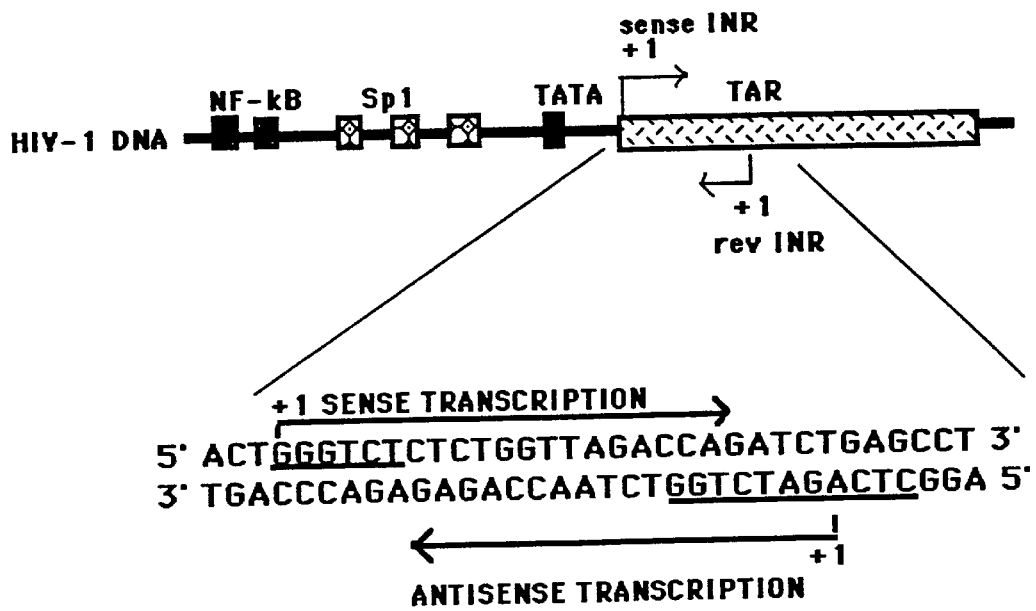
FIG. 2a–2d are a schematic representation of the HIV-1 LTR showing various regulatory elements, bidirectional transcription, and one or more mechanisms by which the antisense transcripts generated from HIV aINR may regulate transcription and/or translation.
Figure 2B:
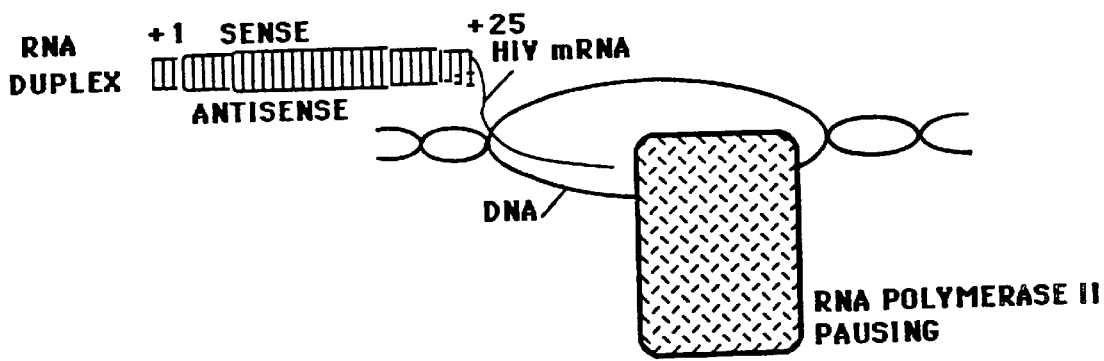
Figure 2C:
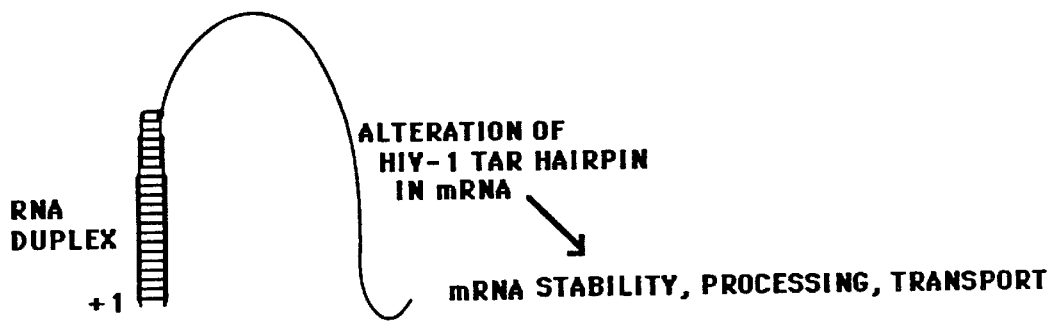
Figure 2D:
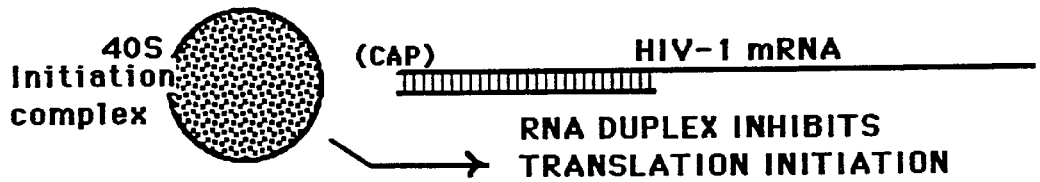

By the terms "antisense initiator sequence" or "aINR" and its "functional equivalent" is meant, for the purposes of the specification or claims, a double-stranded genetic element present in eukaryotic DNA, such as mammalian DNA or viral DNA employing eukaryotic regulatory elements, which (a) when placed in a cis-acting orientation, downstream of and operably linked to a DNA molecule, regulates the expression of a target gene in a mammalian cell;

(b) initiates transcription from the operably-linked DNA molecule into RNA transcripts of negative strand polarity (antisense) that function to specifically bind to, in forming an RNA duplex with, sense RNA transcripts being produced from a target gene; and (c) has a consensus sequence of G/A G/A A/T N T G G/A. In a further embodiment of the present invention, the aINR may comprise an additional nucleotide on the 3' end, an eighth nucleotide, comprising a G or an A. "Cis-acting" refers to the positive strand of the DNA molecule being on the same strand as the consensus sequence of aINR. Additionally, a nucleotide sequence which is identical to the consensus nucleotide sequence of the aINR disclosed in SEQ ID NO:1, except for a base change or substitution, may function substantially (ranging from approximately 50% of the activity to greater than 100% of the activity of SEQ ID NO:1) as SEQ ID NO:1, and thus is a functional equivalent because of the ability to substantially initiate the transcription of a desired DNA molecule in eukaryotic cells.

By the term "operably linked" is meant, for the purposes of the specification and claims to refer to the chemical fusion (restriction with subsequent ligation) or synthesis of DNA such that a DNA molecule-aINR combination is formed in a proper orientation and reading frame for the DNA molecule to be transcribed into functional antisense RNA with the transcription being initiated by the aINR. In the construction of the DNA molecule-aINR combination, it is generally preferred to position the aINR at a distance downstream from the DNA molecule that is approximately the same as the distance in its natural setting. However, as known in the art, some variation in the distance can be accommodated without loss of initiator function. Likewise, additional DNA sequences comprising regulatory elements (e.g., CAAT box or a complementary sequence of a TATA box in reverse orientation) may be positioned downstream of the aINR within a distance shown to be optimal in enhancing initiation from the aINR.

By the terms "consisting essentially of a nucleotide sequence" is meant, for the purposes of the specification or claims, the nucleotide sequence disclosed, and also encompasses nucleotide sequences which are identical except for a one base change or substitution therein.

By the terms "individual" or "host" is meant, for the purposes of the specification and claims to refer to any mammal, especially humans; plants; and viruses utilizing eukaryotic mechanisms of transcription.

By the term "DNA molecule" is meant, for the purposes of the specification and claims to refer to a double stranded (ds) nucleic acid sequence that contains regulatory sequences involved in the initiation and efficiency of transcription of a target gene and/or gene sequences, such that the DNA molecule is transcribed into RNA transcripts of negative strand polarity that function to bind to, in forming an RNA duplex with, sense RNA transcripts being produced from a target gene.

By the terms "plus strand" or "plus strand polarity" is meant, for the purposes of the specification or claims, to refer to a single-stranded (ss) DNA molecule which is selected from the group consisting of coding sequence of a target gene, or the strand of a DNA sequence from which is transcribed mRNA or RNA that is complementary to antisense RNA initiated by an aINR.

By the terms "minus strand" or "negative strand polarity" is meant, for the purposes of the specification or claims, to refer to a single-stranded (ss) nucleic acid molecule which is complementary to the plus strand.

By the term "complementary" is meant, for the purposes of the specification or claims, to refer to a single stranded nucleotide sequence having a sufficient number of pairing bases such that it specifically (non-randomly) hybridizes to another single stranded nucleotide sequence with consequent hydrogen bonding.

By the term "recombinant expression vector" is meant, for the purposes of the specification and claims to refer to a nucleic acid construct (vector sequence) comprising the aINR operably linked to a DNA molecule such that transcription from the AINR is effected in a suitable host. The vector may include, but is not limited to, a plasmid, phage, viral vectors, viral-like vectors, or a potential genomic insert (see, e.g., Mulligan et al., 1993, *Science* 200:926–932).

By the term "regulatory element" is meant, for the purposes of the specification and claims to refer to an upstream promoter element motif which functions to facilitate binding of RNA polymerase or transcription factors in the initiation, activity, and efficiency, of transcription. Eukaryotic regulatory elements include, but are not limited to a TATA box, a TATA-like box (e.g., TTTAA, TTTAAA, TAT, TAATA), a CAAT box, a CAAT-like box (e.g., CTAATC), upstream stimulatory factor (USF), upstream sequence element (USE), and binding sites for transcription factors (e.g., AP-2, SP1, CRE, PEA-3, NF-IL6, etc.).

The ability to impact both normal physiological processes and pathological processes in eukaryotes depends largely upon modulation of gene expression in eukaryotic cells. In analyzing expression of retroviruses and mammalian cells, a novel genetic element, and mechanism of regulation of gene expression from this element, were discovered. This genetic element is not restricted to mammals, however. Since it is also found in retroviruses, it may represent a more universal (i.e., eukaryotic) control mechanism. Isolation and characterization of this genetic element revealed that it comprises a 7 base pair (bp) element which may act to initiate RNA transcripts of negative strand polarity that directly inhibit, via antisense mechanisms, the general transcriptional machinery at the transcriptional initiation site and/or activators necessary for efficient transcription of a gene present in an opposite complementary strand of DNA. In a further embodiment, the genetic element may be extended to 8 base pairs to further enhance function. In a natural setting, and in general, the element may be located in a location selected from the group consisting of between a promoter of positive strand polarity (e.g., the TATA box) and the initial coding region of the gene which it regulates, or within the coding sequence of a gene. This mechanism of transcriptional repression is a natural antisense RNA regulatory system, with a key component of the system comprising an element which has been termed an "antisense initiator sequence" (aINR).

According to one embodiment of the present invention, using recombinant DNA techniques, at least one copy of an aINR and at least one copy of a DNA molecule are operably linked and incorporated into an expression vector. The recombinant vector is then introduced into an appropriate host cell thereby directing the expression of RNA transcripts of negative strand polarity that directly inhibit the general transcriptional machinery at the transcriptional initiation site and/or activators necessary for efficient transcription of the target gene expressed in that particular host cell. This method of transcriptional repression according to the present invention, comprises introducing the recombinant vector into the host cells such that antisense transcripts generated from the aINR may down regulate the expression of a target gene in the host cells. It will be appreciated by those skilled in the art that the recombinant vector can be introduced into the host cells in culture (in vitro), or may be introduced to cells in vivo such as in a gene therapy application.

A more complete appreciation of the invention, and its many attendant advantages thereof, may become apparent by referring to the following Examples which are provided to aid in the understanding of the features of the invention, and to enable one skilled in the art to make and use the novel antisense initiator sequence of the present invention. The following Examples are intended to be illustrative of the invention, and are not to be construed as limiting the scope of the invention.

EXAMPLE 1

An aINR in the human immunodeficiency virus

According to the present invention, an antisense initiator sequence from retroviral DNA was identified and mapped. As shown in FIG. 1, an HIV-1 aINR (SEQ ID NO:2) is situated downstream from the usual HIV-1 promoter and transcription start site. This HIV-1 aINR is located in the 5' LTR (and also in the 3' LTR) R region, and more particularly, in a double-stranded DNA region known as the TAR region. The aINR is located approximately 21–27 nucleotides from the cap site and start site of usual sense HIV-1 transcription; and is oriented to generate a transcript opposite in direction, and complementary to, the beginning of the TAR region of known HIV-1 transcripts. The antisense transcript generated off of the aINR is complementary to at least the initial 25 nucleotides of all HIV-1 sense transcripts, but may comprise a complementary sequence greater than 25 nucleotides in length.

The TAR region, present on a RNA transcript, is bound by Tat resulting in transcriptional activation that dramatically increases the levels of viral mRNAs of plus strand polarity transcribed from the HIV 5' LTR promoter. Both a functional Tat protein and TAR sequence are required for the increase in full-length transcripts observed subsequent to transactivation by Tat, as well as for HIV-1 survival (Cullen, 1992, *Microbiol. Reviews* 375–394). As demonstrated herein, and as illustrated in FIG. 2, this HIV aINR initiates transcription antisense to a portion of the TAR RNA sequence. The HIV aINR DNA contains sequence similar to a portion of the sequence described as comprising the Tat protein binding site in TAR RNA (Weeks et al., 1990, *Science* 249:1281–85). HIV aINR is capable of generating RNA transcripts which can form RNA duplexes with mRNA being transcribed from the HIV-1 sense promoter. Such RNA duplex formation can modulate the effective synthesis of HIV sense primary transcripts, and therefore HIV-1 gene expression, by one or more mechanisms which may include inhibiting or attenuating efficient RNA polymerase II elongation of sense transcripts, affecting the sense MRNA stability or processing in the nucleus, and inhibiting cap site function in initiation of translation (also illustrated in FIG. 2).

Experiments looking at transcription either in vitro or in vivo were performed to demonstrate that this HIV aINR could initiate antisense transcript(s), and that the antisense transcript(s) generated could function to inhibit transcription from a strong bacteriophage promoter.

Bacteriophage transcription system

A bacteriophage transcription system, utilizing an HIV LTR template linked to a bacteriophage promoter, was used to generate antisense RNA, and to demonstrate that antisense transcripts resembling aINR generated RNA could inhibit "sense" transcription in vitro. An HIV-1 LTR doublestranded (ds) DNA template (termed 5'T7HaeIII-3'HindIII-SP6) was generated by pooled amplification reactions (polymerase chain reaction, "PCR") fragment such that the template contained a T7 site on the 5' end. Thus, the 5' end extended from the HIV-1 SP-1 binding site(s) to just beyond the TAR region for a total length of approximately 213 bp. Two other dsDNA templates were also constructed by polymerase chain reaction, and utilized to make purified antisense RNA in vitro in separate reactions: wherein a TAR dsDNA template (SEQ ID NO:3) was designed to make antisense TAR RNA, and an HIVaINR dsDNA template (SEQ ID NO:4) was designed to make antisense HIVaINR RNA. Parallel transcription reactions were set up with buffer reagents as follows:

1: 5'T7HaeIII-3'HindIII-SP6 template+T7 RNA polymerase;
2: 5'T7HaeIII-3'HindIII-SP6 template (negative control);
3: 5'T7HaeIII-3'HindIII-SP6 template+purified antisense TAR RNA (added either 10X or 5X to 5'T7HaeIII-3'HindIII template)+T7 RNA polymerase; and
4: 5'T7HaeIII-3'HindIII template+purified antisense HIVaINR RNA (added either 10X or 5X to 5'T7HaeIII-3'HindIII template)+T7 RNA polymerase.

Figure 3:
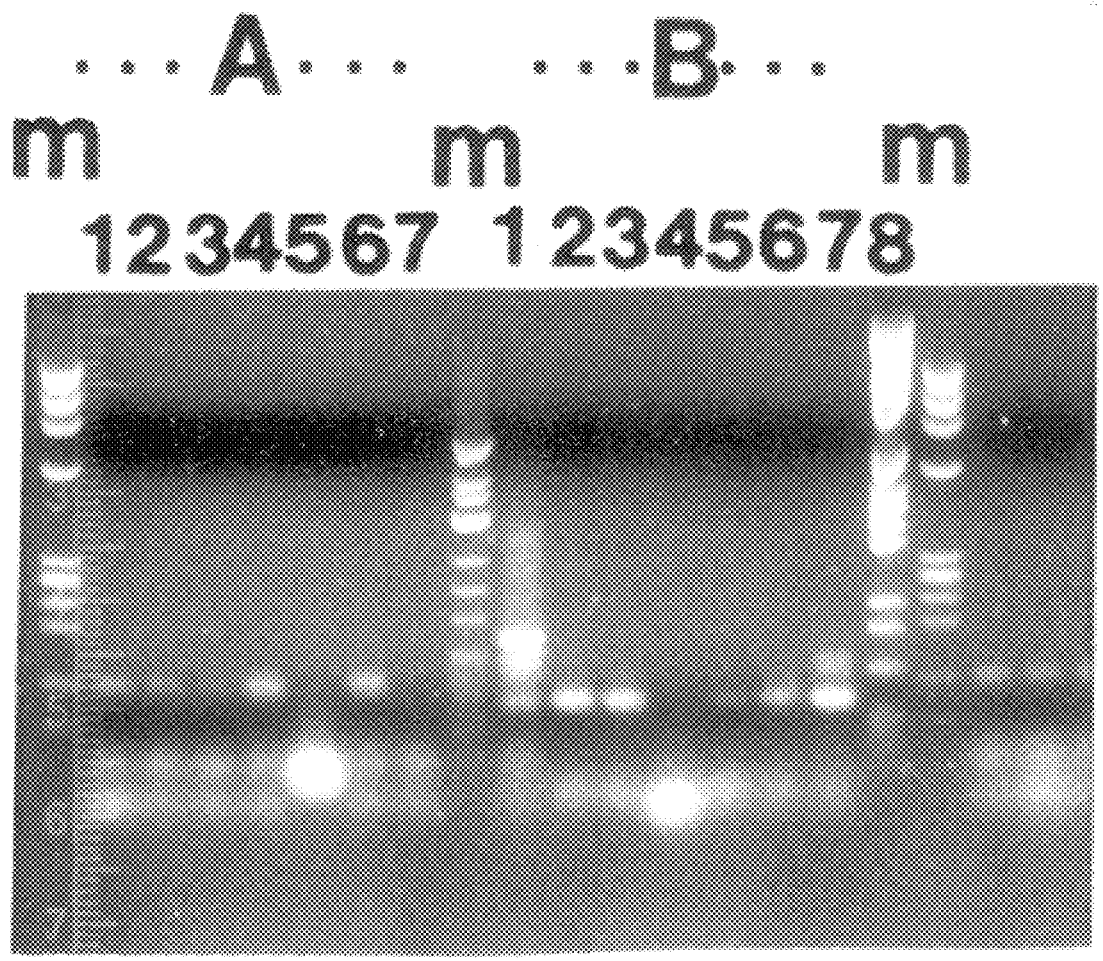
FIG. 3 is a representation of a 2% agarose gel of in vitro transcription reactions followed by primer hybridization with either a sense biotinylated primer (Group A, lanes 1–7) or an antisense primer (Group B, lanes 1–7) with an initial reverse transcription step, followed by polymerase chain reaction. Lanes 1 of groups A and B represent the positive transcription control (template+polymerase); whereas lanes 2 represent the negative transcription control (template without polymerase). Lanes 3 and 4 of group A and lanes 3 and 5 of group B represent transcription in the presence of HIV aINR RNA (10×, and 5×, respectively); whereas lanes 6 and 7 of groups A and B represent transcription in the presence of HIV antisense TAR RNA (10×, and 5×, respectively). Also shown are primers only (group A, lane 5, and group B, lane 4), and size markers for reference.

Following incubation, each of the in vitro transcription reactions were then treated with DNaseI to remove the dsDNA template, followed by phenol-chloroform extraction and by ethanol precipitation to obtain purified synthesized RNA. The purified synthesized RNA from each reaction was then analyzed by reverse transcription-polymerase chain reaction. As illustrated in FIG. 3 representing a 2% agarose gel, the reactions represented in Group A, lanes 1–7, were analyzed by a "sense" biotinylated primer (5' SpI-IIB) in the initial reverse transcription step, followed by polymerase chain reaction using a 5' SpI-IIB primer and a 3' T7 primer (LTR sequence, nucleotides 442–477). Thus, the lanes in Group A would detect RNA transcripts of negative strand polarity oriented in the antisense direction. Since T7 RNA polymerase can synthesize RNA transcripts only in the sense direction off of the 5'T7HaeIII-3'HindIIISp6 template, the lanes in Group A appropriately show no reverse transcription PCR products produced (i.e. showing only the primers, and primer dimers). As illustrated in FIG. 3, the reactions represented in Group B, lanes 1–7, were analyzed by an "antisense" biotinylated primer (3'HindIII-B) in the initial reverse transcription step, followed by polymerase chain reaction using a 5'R primer and a 3'HindIII-B primer. Thus, the lanes in Group B detect RNA transcripts, synthesized by T7 RNA polymerase, oriented in the sense direction. Group B, lane 1 shows RNA transcripts resulting from the in vitro transcription reaction containing 5'T7HaeIII-3'HindIII template+T7 RNA polymerase, followed by analysis using reverse transcription polymerase chain reaction. Appropriately, this lane shows reverse transcription PCR products generated from RNA transcripts made from this reaction (while also showing primer, and primer dimers). Group B, lane 2 appropriately shows no transcripts were produced in the in vitro transcription reaction containing 5'T7HaeIII-3'HindIII template only (negative control without T7 RNA polymerase). Group B, lanes 3 (10X) and 5 (5X) demonstrate that the presence of antisense HIV aINR RNA transcripts in the in vitro transcription reaction inhibited in vitro transcription of the 5'T7HaeIII-3'HindIII template by T7 RNA polymerase. Similarly, Group B, lanes 6 (10X) and 7 (5X) demonstrate that the presence of antisense TAR RNA during in vitro transcription of the 5'T7HaeIII-3'HindIII template inhibited synthesis of RNA by T7 RNA polymerase.

In summary, this in vitro transcription assay shows that antisense RNA transcripts extending from HIV aINR can inhibit the production of sense HIV RNA transcripts, even from a strong promoter such as the T7 bacteriophage promoter.

Drosophila in vitro transcription system

This eukaryotic transcription system uses Drosophila embryo nuclear extracts to supply transcription factors and RNA polymerase II; and demonstrates that the HIV aINR functions within its own promoter context. This in vitro system was used as a model for the process in vivo, since once HIV is integrated into human host T cell chromosomal DNA, it is dependent upon eukaryotic transcription factors and RNA polymerase II to transcribe its genes.

A. RNase Protection Assay

Figure 4:
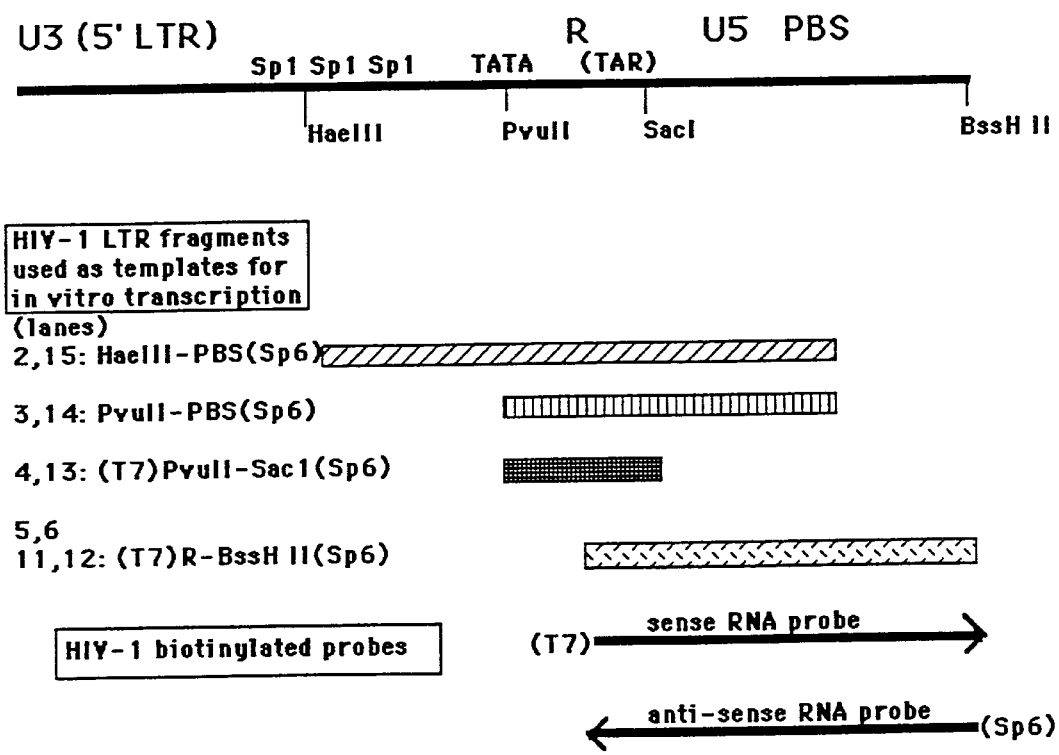
FIG. 4 are schematic diagrams of the 5' LTR of HIV, truncated dsDNA templates derived therefrom, and probes for in vitro transcriptions followed by RNase protection assays.

A eukaryotic transcription system (a commercial Drosophila embryo nuclear extract transcription system) that can efficiently transcribe from eukaryotic initiators in vitro was used to investigate whether eukaryotic transcription could initiate from the HIV aINR. Four different HIV-1 LTR fragments were generated by polymerase chain reaction using HIV-LTR template and primers containing specific HIV-1 sequences and promoter sequences for bacteriophage T7 or SP6 RNA polymerases, as previously described (Ludwig et al., 1995, Nucleic Acids Res. 23:3792–93). As shown in FIG. 4, the four truncated dsDNA templates for in vitro transcription include the 5'HaeIII-PBS(SP6)3' template having two Sp1 sites and the TATA box; the 5'PvuII-PBS (SP6)3' template lacking all of the Sp1 sites and bisecting the TATA box; the 5'(T7)PvuII-SacI(SP6)3' template truncating the TAR region 48 bp from the mRNA cap site and start site; and the 5'(T7)R-BssHII(SP6)3' template containing no HIV-1 promoter Sp1 sites nor a TATA box.

In vitro transcription reactions were performed with each template and with Drosophia nuclear extract, essentially using conditions according to the manufacturer's instructions. Each of the in vitro transcription reactions were then treated with DNaseI to remove the DNA template, followed by phenol-chloroform extraction and by ethanol precipitation to remove the DNase from the synthesized RNA. The purified synthesized RNA from each reaction was then analyzed by an RNase protection assay, performed essentially as described by the kit's manufacturer, with the exception of using biotinylated RNA probes for hybridizations followed by RNase T1 digestions. The biotinylated RNA probes were synthesized in vitro using either T7 RNA polymerase (for the sense probe) or SP6 RNA polymerase (for the antisense probe), as previously described (Ludwig et ale, 1995, supra). As shown in FIG. 4, the biotinylated sense probe contained HIV-1 sequences extending from the cap site to the BssHII site, and thus includes the TAR region. The hybridized and protected fragments were then analyzed by electrophoresis in an 8% denaturing gel, followed by membrane transfer and colorimetric detection (Ludwig et al., 1995, supra).

Figure 5:
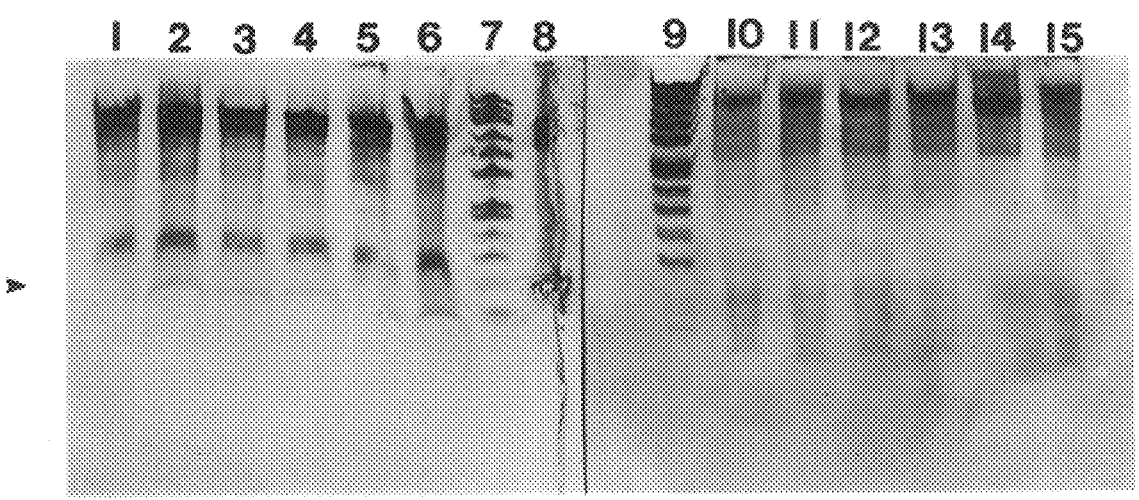
FIG. 5 is a representation of the results of eukaryotic transcription reactions in vitro subjected to the RNase protection assay, with RNA protected fragments analyzed by electrophoresis in an 8% denaturing gel, followed by membrane transfer and calorimetric detection. Lane 1 is a control RNase digestion assay hybridized with the biotinylated sense probe; lanes 2–6 represent the variably sized templates illustrated in FIG. 4 used in in vitro transcription assays, hybridized with the biotinylated sense probe, and followed by RNase digestion; lane 10 is a control RNase digestion assay hybridized with the biotinylated antisense probe; and lanes 11–15 represent the variably sized templates illustrated in FIG. 4 used in in vitro transcription assays, hybridized with the biotinylated antisense probe, and followed by RNase digestion. Lanes 7 and 9 are size markers for reference.

As shown in FIG. 5, lanes 10–15, no transcripts were initiated in the usual sense orientation, as the RNAse digestion assay demonstrated that the antisense probe failed to hybridize, and thereby protect, sense transcripts. Compare the control RNase digestion with antisense probe plus tRNA (lane 10) with lanes 11–15 (antisense probe+sample RNA (s)). It is important to note that the Drosophila extracts used in this assay intrinsically lacked Sp1 protein. Thus, a major driving force for sense transcription of any of the templates containing a SP1 site was lacking, allowing for observance of antisense transcription in isolation. All four templates contained the HIV aINR in the TAR region DNA. If antisense transcription was initiated by the HIV aINR, the expected region of overlap for complementary base pairing between the transcripts with the sense probe (and the expected size of RNA protected by hybridization) would be 26–28 nucleotides, depending on the template. Despite the large amount of secondary structure in the biotinylated sense probe (lane 1, control RNase digestion with sense probe+ tRNA), protected HIV aINR generated antisense transcripts of the expected size (see arrow) were detected as shown in FIG. 5, lanes 2–6. No antisense transcript was observed using ds DNA templates lacking the HIV aINR in this in vitro transcription assay (results not shown). By progressively truncating the HIV-1 LTR region used as templates for the in vitro transcription reactions, a minimal aINR was mapped.

In summary, this in vitro eukaryotic transcription system, coupled with an RNase protection assay, shows that the HIV aINR can generate transcripts opposite in direction and complementary to (e.g., antisense to) HIV-1 sense RNA transcripts containing the TAR region sequence.

B. Primer Extension

Figure 6:
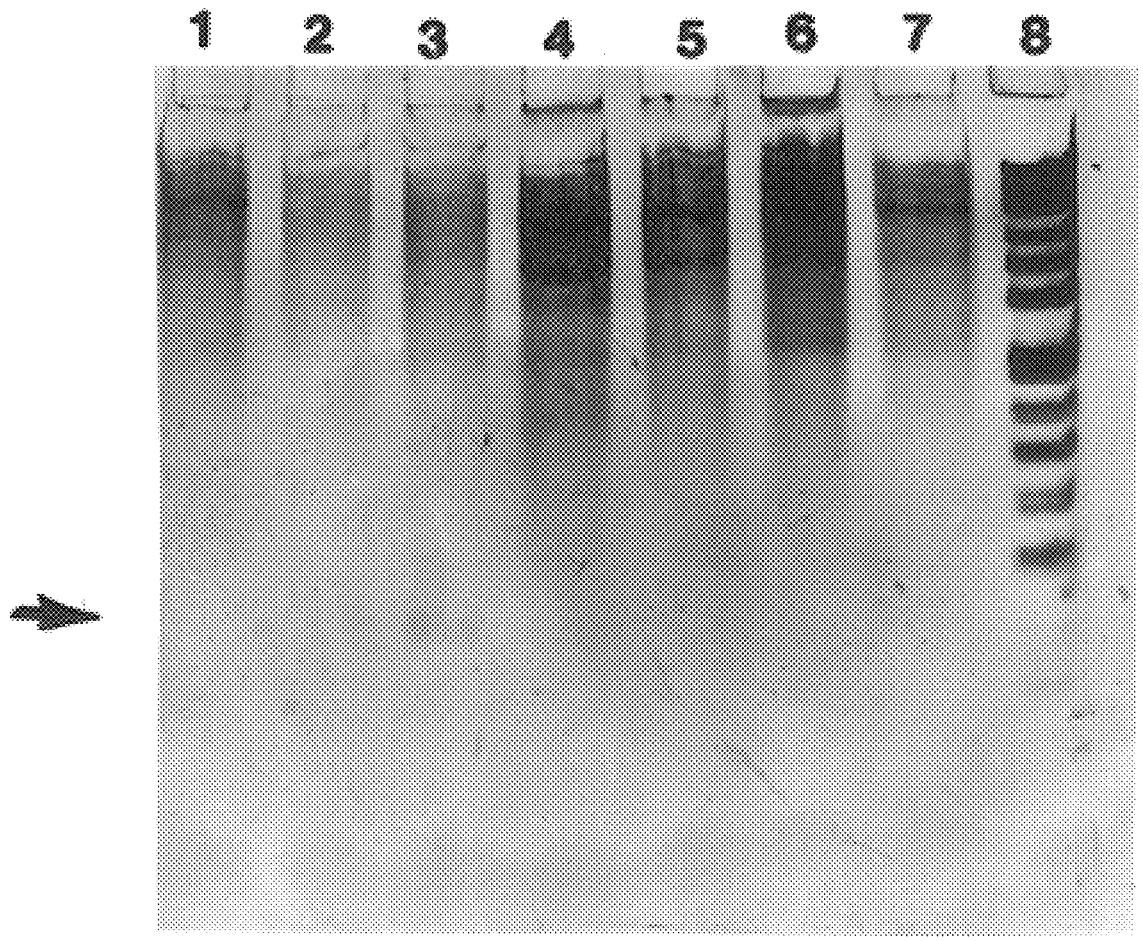
FIG. 6 is a representation of the results of a primer extension assay of eukaryotic transcription reactions analyzed by electrophoresis in an 8% denaturing gel, followed by membrane transfer and calorimetric detection. Lane 1 is a nuclear extract control (in vitro transcription performed without added DNA template and then analyzed by primer extension); lane 2 represents cDNA made from RNA generated by the HIV aINR, following hybridization and extension with the antisense probe (negative control for antisense RNA); and lane 3 represents RNA generated by the HIV aINR hybridized and extended with the sense probe.

Using the in vitro eukaryotic transcription system and the 5'(T7)PvuII-SacI(SP6)3' HIV-1 template (dsDNA), any RNA transcripts present (following DNAse digestion, phenol chloroform extraction and ethanol precipitation) were analyzed by primer extension. Primer extension was performed using unlabeled primers, but incorporating biotin-16-dUTP during the AMV reverse transcriptase-mediated cDNA synthesis reaction. As shown in FIG. 6, the large molecular weight species apparent in all lanes was contributed by the Drosophila nuclear extract (see, lane 1, nuclear extract control in which in vitro transcription was performed without added DNA template and then analyzed by primer extension). As also shown in FIG. 6, primer extension of the purified RNA demonstrated a cDNA product of the expected size (arrow, lane 3) from RNA generated by the HIV aINR and extended with the sense primer (5'(T7)PvuII); but not with an antisense primer (3'SacI-SP6) (lane 2).

In summary, this in vitro eukaryotic transcription system, coupled with a primer extension assay to analyze the RNA transcribed in vitro, shows that the HIV aINR can function to initiate antisense transcripts even in the absence of the usual "sense" HIV-1 promoter elements.

In vivo transcription system

It was particularly important to demonstrate that this HIV aINR could direct the production of antisense transcripts in vivo. In vivo transcription from the HIV aINR was analyzed by reverse transcriptase-PCR of RNA isolated from human Jurkat T cells which had been transfected with PHIV-CAT, and as compared to transfection controls. Plasmid PHIV-CAT contains the HIV-1 LTR U3 and R sequences 5' to the chloramphenicol acetyltrans-ferase (CAT) gene. Transfections of plasmid DNA were performed in the presence of a transfection reagent (Transfectam, Promega) that enhances plasmid uptake by cells. In a well of a 96 well microtiter plate, $3.8\times10^5$ cells were mixed with the plasmid DNA (0.086 µg plasmid DNA per 0.182 µl transfection reagent) and incubated for 2 hours using conditions as essentially described by the manufacturer. Control transfection reactions included pHIV-CAT plus pSV-βgal plus transfection reagent (to assess transfection efficiency), transfection reagent alone (no plasmid DNA; "mock transfected"), or receiving no treatment at all. The cells from the respective transfection reactions were then resuspended in culture medium and carried in culture for two days. RNA was then extracted from the cultured cells using methods and reagents known in the art. The extracted RNA was purified and isolated, and then the sample RNAs were subjected to reverse transcription using a 5'AvaI sense primer (containing sequences upstream of the HIV-1 LTR enhancer elements), followed by amplification by polymerase chain reaction for 30 cycles of denaturing (94° C., 45 seconds), reannealing (70° C., 45 seconds), and extension (72° C., 2 minutes) using the 5'AvaI sense primer, and a 3'antisense primer (SEQ ID NO:9) containing sequences complementary to beginning TAR sequences. The reverse transcription-PCR products were then analyzed by electrophoresis on 3% agarose gels. The results are illustrated in FIG. 7.

Figure 7:
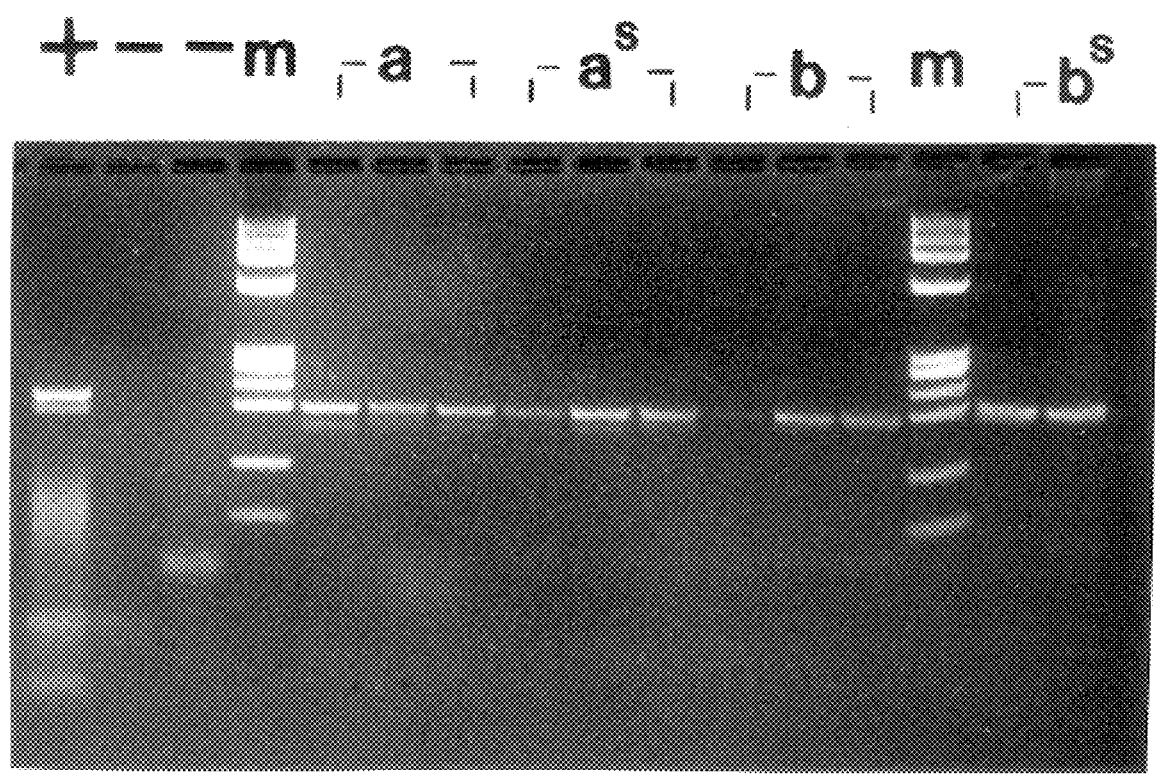
FIG. 7 is a representation of the results of in vivo eukaryotic transcription reactions in assaying for antisense RNA generated from the HIV aINR, as analyzed by reverse transcriptionpolymerase chain reaction, followed by agarose gel electrophoresis.

In FIG. 7, lanes marked "m" represent the DNA size standard markers. The positive RT-PCR control (FIG. 7, lane "+") represents use of the AvaI primer in the reverse transcription step followed by use of the 5'AvaI sense primer and a 3' antisense primer designed to amplify a control antisense RNA template, synthesized as described previously (Ludwig et al., 1995, supra). The negative control reverse transcription-PCR reaction (FIG. 7, lanes "−") shows no amplified product (faint bands represent primer) which indicates that there was no DNA (pHIV-CAT) contamination of the purified RNA samples. dsDNA products of the expected size of 183 bp, amplified from the HIV-1 antisense transcripts, were clearly visible (FIG. 7, shown in triplicate, lanes "a": pHIV-CAT with transfection control plasmid pSVgal; and lanes "b": pHIV-CAT). Lanes marked with an "s" represent stimulation of transfected T cells with PMA (phorbol-12-myristate 13-acetate) and a calcium ionophore (T cell activators) following transfection with the indicated plasmids.

Regardless of the presence or absence of stimulation, it is clear that HIV-1 antisense RNA was generated in vivo from the HIV aINR in human T cells. Data to date (not shown) suggests that antisense RNA generated in vivo from the HIV aINR in transfected human T cells represents a significant portion of the total RNA generated off of the HIV-1 LTR in the absence of TAT.

EXAMPLE 2

Mammalian aINRs

According to the present invention, antisense initiator sequences may be, and have been, found in regions positioned to regulate expression of mammalian genes by the generation of antisense transcripts. For example, a transcriptional silencer comprises a negative regulatory element which could be positioned between the enhancer and promoter of the CD4 gene (or transgene) or between the promoter and the gene, thereby being positioned (as in its natural setting) downstream of the CD4 transcription initiation site (Sawada et al., 1994, *Cell* 77:917–29, herein incorporated by reference) This transcriptional silencer, the CD4 silencer, was narrowed down to a 428 bp restriction fragment located about 2 kb downstream of the transcriptional initiation site; thus, the transcriptional silencer can function up to a distance of at least 2 kb from the initiation site of the gene which it represses. According to the present invention, discovered in the 428 bp CD4 silencer is at least one aINR (SEQ ID NO:5) located between 183–191 of the sequence. The mechanism of transcriptional repression of the CD4 gene models that observed with the HIV LTR. For example, the CD4 gene expression appears to be transcriptionally repressed in DN (CD4−, CD8−) thymocytes, but is upregulated in the progression of DN thymocytes to the DP stage (CD4+, CD8+) which may be a result of an inactivation of the repressor/silencer mechanism. Likewise, it appears that the transcriptional repression of the HIV LTR promoter, as may be mediated by the HIV aINR, is rendered inefficient (either inactivated or reduced to a low basal level inefficient for transcriptional repression of the HIV LTR promoter) by the binding of Tat to TAR.

In another example, and in a report of the repression of expression of the T cell receptor γ gene (TCRγ) in TCRαβ+ cells, a region containing multiple transcriptional silencers was identified (Lefranc and Alexandre, 1995, *Eur. J. Immunol.* 25:617–22, herein incorporated by reference). The transcriptional silencers, flanking the TCRγ gene, are contained in a 1.2 kb SacI B fragment. The data indicated that the silencing of the TCRγ locus in TCRαβ+ cells is mediated by transcriptionally active silencers. According to the present invention, discovered in the 1.2 kb TCRγ silencer is at least one aINR (SEQ ID NO:6) located as nucleotides 853–859 of the sequence of the silencer-containing B fragment.

In a further example, and in a report of the repression of expression of the T cell receptor α gene (TCRα) in TCRγδ cells, a region containing multiple transcriptional silencers was identified (Winoto and Baltimore, 1989, *Cell* 59:649–55, herein incorporated by reference). Further, this report provides a brief review of previously described negative regulatory elements that repress transcription independent of orientation and distance from the promoter/enhancer ("independent" as determined by placing a substantial fragment containing the element in different positions and orientation which would not affect the immediate transcription therefrom). Two TCRA transcriptional silencers were each localized to respective 300+bp fragments. For example, and according to the present invention, discovered in the 309 bp TCRα transcriptional silencer SIL I is at least one aINR (SEQ ID NO:7) located as nucleotides 85–92 of the sequence of SIL I.

Table 1 illustrates a comparison of various aINR sequences, and with the consensus sequence derived according to the present invention.

TABLE 1

| SEQ ID NO | Base position in aINR sequence | | | | | | | |
|---|---|---|---|---|---|---|---|---|
|  | 1 | 2 | 3 | 4 | 5 | 6 | 7 | 8 (optional) |
| 1 consensus | G/A | G/A | A/T | N | T | G | G/A |  |
| 2 | G | A | T | C | T | G | A | G |
| 5 | A | G | A | G | T | G | G | G |
| 6 | A | A | T | A | T | G | G |  |
| 7 | A | G | T | C | T | G | G | G |

N= A, T, G, or C

Having identified a consensus aINR sequence, a process of making an aINR or a nucleic acid sequence containing the aINR can be performed using standard methods known in the art. For example, enzymatic nucleic acid amplification may be used to amplify the aINR from a nucleic acid sequence containing the aINR, followed by purification of the amplified product comprising the aINR. Another method is the use of a nucleic acid synthesizer, and the related standard biochemical techniques, in which the aINR can be chemically synthesized.

EXAMPLE 3

Recombinant vectors containing aINR(s)

In accordance with the present invention, compositions and methods of modulating gene expression are provided. A vector may be constructed which contains at least one copy of an aINR downstream of and operably linked to in cis at least one copy of a DNA molecule having the sequence to be regulated. Downstream of the aINR sequence may be placed one or more regulatory elements (e.g., CAT box, TATA box) in proximity (as known to those skilled in the art) so as to function with the aINR in signaling and initiating transcription of antisense transcripts. The resultant recombinant vector is then introduced into cells expressing the target gene to be modulated. Once in the cells, from the recombinant vector the aINR initiates production of antisense RNA transcripts. The antisense RNA transcripts then modulate the expression of the target gene by forming RNA duplexes with the sense mRNA being transcribed from the target gene. Alternatively, triplex formation could occur between the dsDNA of the target gene and the antisense RNA transcripts. Since transcription of the target gene is inhibited, there are few, if any, full-length sense mRNA transcripts available to be translated into the protein encoded by the target gene. Therefore, such modulation may result in a decrease in the amount of such protein produced by the treated cells.

There are several considerations in making such a vector.

A. Base construct

Vectors, used in accordance with the present invention as a vehicle for introducing into the host cell and generating antisense transcripts from the aINR incorporated therein, can be selected from plasmids, viruses, retroviruses, phage, or to be integrated as a chromosomal insert. It will be appreciated by those skilled in the art that the general features of the base vector may vary depending on such factors including, but not limited to, whether the subsequent recombinant vector is to be introduced into host cells in vitro or in vivo, and whether the gene expression to be regulated is of a gene in single or multiple copies (e.g., in which case the copy number of the vector may be a considered variable). However, some basic features of a vector which make it useful in the methods of the present invention include that it have a selection marker for identifying host cells which have been transfected by the vector; and restriction sites to facilitate cloning of the at least one copy of the aINR downstream of and operably linked in cis to the at least one copy of the DNA molecule in forming the recombinant vector. Additionally, in certain circumstances, it may be desirable to also provide a mechanism by which the aINR can be "turned off" or repressed such that antisense transcripts are no longer generated by the aINR.

Examples of available and useful base vectors are known to those skilled in the art and include, but are not limited to, plasmids pRSVneo, pSV2gpt, pSV2neo, and pCMV. Particularly useful for delivering genes or DNA molecules into mammalian cells either in vitro or in vivo are a variety of viral vectors including, but not limited to, retroviral vectors, adenovirus vectors, adeno-associated virus (AAV) vectors, herpes virus vectors, vaccinia virus vectors, polio virus vectors, and Sindbis and other RNA viruses (as, for example, reviewed by Mulligan, 1993, *Science* 260:926–932).

For example, one preferred vector for gene therapy applications is a parvovirus vector which allows stable, site-specific integration of a transferred recombinant DNA molecule. Since AAV is not presently associated with any known human disease, a vector made up of AAV or a hybrid parvovirus vector appears safe for use such as in gene therapy applications (see for example Chatterjee et al., 1992, *Science*, 258:1485–1488; U.S. Pat. No. 5,252,470 to Srivastava). In such an AAV vector, a promoter in the ITR (inverted terminal repeats) can drive the expression of the neomycin phosphotransferase gene or other marker gene, whereas the aINR drives transcription into antisense RNA. The ITR of the AAV vector also provide a means for integrating the vector, and sequences inserted therein, into the chromosome as the ITR serves as a sequence which has been shown to insert site-specifically, rather than randomly, into chromosomes. Another preferred vector is a replication-deficient adenovirus that has one or more genes necessary for replication deleted (such as E1A–E1B and E3 regions).

B. Recombinant vector construction

Using methods standard in the art, at least one copy of aINR is downstream of and operably linked in cis to at least one copy of a DNA molecule having a sequence involved in the initiation of, or elongation of, transcription of a target gene. (the sequence to be regulated). Downstream of the aINR sequence may be placed one or more regulatory elements (e.g., CAT box, TATA box in reverse orientation) in proximity (as known to those skilled in the art) so as to function with the aINR in signaling and initiating transcription of antisense transcripts. Both the aINR and DNA molecule are inserted into, and ligated to a base vector in forming a recombinant vector according to the present invention. To confirm proper construction of the recombinant vector, standard methods can be used, such as analyzing the orientation of insertion into the vector using restriction enzyme digestion and agarose gel electrophoresis, and/or dideoxy sequencing analysis.

It will be appreciated by those skilled in the art that the number of copies of aINR operably linked to the DNA molecule in a recombinant vector may vary depending on the gene expression sought to be regulated. For example, in HIV, to overcome Tat inactivation of the transcriptional repression of the HIV LTR promoter mediated by the HIV aINR, multiple copies (e.g., 10 to 50 or more) of the DNA molecule-HIV aINR combination may be desirable. Additionally, if the gene expression to be regulated is of a gene in single or multiple copies, or is transcribed with relatively high efficiency (i.e., from a strong promoter and enhancer combination known to those skilled in the art), then multiple copies (e.g., 10 to 50 or more) of the DNA molecule-HIV aINR combination may be desirable. Further, while it appears that some aINRs initiate transcription in several cell types, it is possible that an aINR may be affected by proximal regulatory elements that function in a cell-specific manner or may function at a low level in certain cell types (see, for example, transcriptional silencers identified by Winoto and Baltimore, 1989, supra). Thus, multiple copies of the DNA molecule-HIV aINR combination, in conjunction with the function of the regulatory element placed to enhance aINR transcriptional initiation activity, may be necessary to regulate the target gene expression in cells in which a single copy of the particular aINR used is not optimally efficient in initiating transcription for gene regulation. As an alternative, by looking at published sequences of genes which appear to be regulated in a cell-specific manner, aINRs may be identified (by position and consensus sequence), along with the appropriate regulatory element (by position and consensus sequence) which will function in that particular cell type.

As an illustration of this embodiment according to the present invention, a recombinant vector is constructed by ligating into a base vector 10 to 50 copies of a sequence comprising a DNA molecule-HIV aINR combination for gene regulation of the HIV 5' LTR. In a preferred embodiment, to increase efficiency of production of antisense transcripts, the sequence comprises a DNA molecule-HIV aINR-regulatory element combination. An exemplary DNA molecule-HIV aINR-regulatory element combination is shown in SEQ ID NO:8. The resultant recombinant vector is then introduced into mammalian cells, and the aINR initiates production of antisense RNA transcripts. The antisense RNA transcripts then modulate the expression of the HIV-1 LTR of HIV-1 contained within the cell by forming RNA duplexes with the sense MRNA being transcribed from the HIV-1 LTR.

In another embodiment, in which the HIV aINR is used in conjunction with a DNA molecule to regulate the expression of a mammalian cellular gene, a mechanism that utilizes the same control mechanism as demonstrated for the HIV 5' LTR can be included as a means for controlling the transcriptional repression mediated by HIV aINR generated antisense transcripts. In this embodiment, the recombinant construct contains an insert comprising the HIV aINR within the intact TAR region DNA (nucleotides 75 to 133 of SEQ ID NO:8) downstream of an operably linked to at least one copy of a DNA molecule containing a target eukaryotic gene, from which antisense can be generated to bind to the sense RNA transcribed from the target eukaryotic gene. In addition, appropriate regulatory elements may be located downstream of the HIV aINR. Such a construct provides a Tat control mechanism. In the absence of Tat in the cell containing the recombinant vector, the HIV aINR generates antisense transcripts which then bind to the sense RNA transcribed from the target gene. In the presence of Tat, such as by subsequently introducing a Tat-expressing vector, transcription of antisense RNA mediated by the HIV aINR may be rendered inefficient (either inactivated or reduced to a low basal level inefficient for transcriptional repression of the target gene) by the binding of Tat to TAR. pTAT vectors have been previously described (Koken et al., 1994 *Gene* 144:243–7; Ho et al., 1990, *J. Gen. Virol.* 71:97–103).

C. Introduction of the recombinant vectors into host cells

Methods of introducing the recombinant vectors into host cells are known to those skilled in the art, and include, but are not limited to, transformation, transfection, calcium phosphate precipitation, microinjection, targeted liposomes, particle-gun bombardment, electroporation, electro-fusion, and infection. Thus, a method according to the present invention for regulating the expression of a target gene in a host cell comprises introducing into the host cell a recombinant vector comprising at least one copy of an aINR (preferably with downstream regulatory elements) operably linked to the at least one copy of the DNA molecule containing the target gene from which antisense RNA is generated, wherein the antisense RNA then binds to the sense RNA transcribed from the target gene thereby regulating the gene expression at the transcriptional and/or translational level.

In another variation of this embodiment, introduction of a recombinant vector comprising the at least one copy of an aINR operably linked to the at least one copy of the DNA molecule, or genetic material comprising at least one copy of an aINR operably linked to the at least one copy of the DNA molecule, may be injected (through any parental route such as intravenous, intraperitoneal, intradermal, subcutaneous, or intramuscular; or via contact with mucosal surfaces of the nasopharynx, trachea, or gastrointestinal tract) directly into an individual ("direct nucleic acid transfer"). Direct nucleic acid transfer into a "vaccinated" individual, resulting in expression of the genetic material by the vaccinated individual's cells such as vascular endothelial cells as well as the tissue of the major organs, has been demonstrated by techniques in the art such as by injecting intravenously an expression plasmid:cationic liposome complex (Zhu et al., 1993, *Science* 261:209–211; herein incorporated by reference). Additionally, a composition comprising the recombinant vector or genetic material of the present invention to be injected may further comprise one or more pharmaceutically acceptable carriers such as a diluent, and/or a compound which increases the uptake of nucleic acid by the cells (referred to as "nucleic acid uptake enhancers").

In another example of this method according to the present invention, cells removed from an individual can be transfected or electroporated by standard procedures known in the art, resulting in the introduction of the recombinant vector (comprising the at least one copy of the aINR operably linked to the at least one copy of the DNA molecule) into the target cell. Cells containing the recombinant vector may then be selected for using methods known in the art such as via a selection marker expressed in the vector, and the selected cells may then be re-introduced into the individual.

From the foregoing, it will be obvious to those skilled in the art that various modifications in the above-described methods, constructs and cells can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, and all changes which come within the meaning and range of equivalency of the claims are therefore intended to be embraced therein.

What is claimed is:

1. An isolated and purified nucleic acid molecule comprising an antisense initiator sequence selected from the group consisting of SEQ ID NO:1, and a sequence which differs from the sequence disclosed in SEQ ID NO:1 by one base, wherein the antisense initiator sequence functions as an antisense initiator for transcription from a DNA sequence located on the same strand as and upstream of the antisense initiator sequence.

2. The nucleic acid molecule according to claim 1, wherein the antisense initiator sequence is selected from the group consisting of SEQ ID NO:2, SEQ ID NO:5, SEQ ID NO:6, SEQ ID NO:7, and a sequence which differs from SEQ ID NO:2, SEQ ID NO:5, SEQ ID NO:6, or SEQ ID NO:7 by one base.

3. A recombinant nucleic acid molecule comprising:
   (a) at least one copy of an antisense initiator sequence according to claim 1; and (b) at least one copy of a DNA molecule, wherein the antisense initiator sequence is downstream of the DNA molecule and in a cis-orientation with respect to a sequence to be regulated in the DNA molecule, wherein the antisense initiator sequence and the DNA molecule are operably linked.

4. The recombinant nucleic acid molecule according to claim 3, further comprising at least one regulatory element that is located downstream of the antisense initiator sequence to enhance initiation of transcription from the antisense initiator sequence.

5. The recombinant nucleic acid molecule according to claim 4, containing a nucleotide sequence selected from the group consisting of SEQ ID NO:8, and a sequence which differs from SEQ ID NO:8 by one base.

6. The nucleic acid molecule according to claim 3, wherein said antisense initiator sequence is selected from the group consisting of SEQ ID NO:2, SEQ ID NO:5, SEQ ID NO:6, SEQ ID NO:7, and a sequence which differs from SEQ ID NO:2, SEQ ID NO:5, SEQ ID NO:6, or SEQ ID NO:7 by one base.

7. A recombinant vector comprising at least one copy of the antisense initiator sequence according to claim 1 downstream of and operably linked to at least one copy of a DNA molecule to be transcribed into antisense RNA, wherein the vector replicates when introduced into an eukaryotic cell.

8. The recombinant vector according to claim 7, further comprising at least one regulatory element that is located downstream of the antisense initiator sequence to enhance initiation of transcription from the antisense initiator sequence.

9. The nucleic acid molecule according to claim 7, wherein said antisense initiator sequence is selected from the group consisting of SEQ ID NO:2, SEQ ID NO:5, SEQ ID NO:6, SEQ ID NO:7, and a sequence which differs from SEQ ID NO:2, SEQ ID NO:5, SEQ ID NO:6, or SEQ ID NO:7 by one base.

10. The recombinant vector according to claim 7, wherein said recombinant vector contains a selectable marker.

11. The recombinant vector according to claim 8, wherein said recombinant vector contains a selectable marker.

12. The recombinant vector according to claim 7, wherein said antisense initiator sequence operably linked to the DNA molecule is represented by the nucleotide sequence selected from the group consisting of SEQ ID NO:8, and a sequence which differs from SEQ ID NO:8 by one base.

13. A eukaryotic cell which contains the recombinant vector of claim 7.

14. A eukaryotic cell which contains the recombinant vector of claim 8.

15. A eukaryotic cell which contains the recombinant vector of claim 9.

16. A eukaryotic cell which contains the recombinant vector of claim 10.

17. A eukaryotic cell which contains the recombinant vector of claim 11.

18. A eukaryotic cell which contains the recombinant vector of claim 12.

19. An RNA molecule made from the recombinant vector according to claim 12.

20. A process of making an antisense initiator sequence of claim 1, wherein said process is selected from the group consisting of using enzymatic nucleic acid amplification to amplify the antisense initiator sequence from a nucleic acid sequence containing the antisense initiator sequence and subsequently purifying the amplified product comprising the antisense initiator sequence, and chemically synthesizing the antisense initiator sequence.

21. A method for regulating the expression of a target gene in a eukaryotic cell which comprises introducing a recombinant vector according to claim 7 into the cells expressing the target gene to be regulated, wherein the antisense initiator sequence of the recombinant vector initiates transcription from the operably-linked DNA molecule into RNA transcripts of negative strand polarity that function to bind to, in forming an RNA duplex with, sense RNA transcripts being produced from the target gene to be regulated, thereby repressing the expression of the target gene.

22. A method for regulating the expression of a target gene in a eukaryotic cell which comprises introducing a recombinant vector according to claim 8 into the cells expressing the target gene to be regulated, wherein the antisense initiator sequence and downstream regulatory element of the recombinant vector initiate transcription from the operably-linked DNA molecule into RNA transcripts of negative strand polarity that function to bind to, in forming an RNA duplex with, sense RNA transcripts being produced from the target gene to be regulated, thereby repressing the expression of the target gene.

23. A method for regulating the expression of a target gene in a mammalian cell which comprises introducing a recombinant nucleic acid molecule according to claim 3 into mammalian cells expressing the target gene to be regulated, wherein the antisense initiator sequence of the recombinant nucleic acid molecule initiates transcription from the operably-linked DNA molecule into RNA transcripts of negative strand polarity that function to bind to, in forming an RNA duplex with, sense RNA transcripts being produced from the target gene to be regulated, thereby repressing the expression of the target gene.

24. A method for regulating the expression of a target gene in a mammalian cell which comprises introducing a recombinant nucleic acid molecule according to claim 4 into mammalian cells expressing the target gene to be regulated, wherein the antisense initiator sequence and the downstream regulatory element of the recombinant nucleic acid molecule initiate transcription from the operably-linked DNA molecule into RNA transcripts of negative strand polarity that function to bind to, in forming an RNA duplex with, sense RNA transcripts being produced from the target gene to be regulated, thereby repressing the expression of the target gene.

25. A method for regulating the expression of a target gene in a mammalian cell which comprises introducing a recombinant nucleic acid molecule according to claim 5 into mammalian cells expressing the target gene to be regulated, wherein the antisense initiator sequence and the downstream regulatory element of the recombinant nucleic acid molecule initiate transcription from the operably-linked DNA molecule into RNA transcripts of negative strand polarity that function to bind to, in forming an RNA duplex with, sense RNA transcripts being produced from the target gene to be regulated, thereby repressing the expression of the target gene.

26. The method according to claim 21, wherein said antisense initiator sequence is selected from the group consisting of SEQ ID NO:2, SEQ ID NO:5, SEQ ID NO:6, SEQ ID NO:7, and a sequence which differs from SEQ ID NO:2, SEQ ID NO:5, SEQ ID NO:6, or SEQ ID NO:7 by one base.

27. The method according to claim 22, wherein said antisense initiator sequence is selected from the group consisting of SEQ ID NO:2, SEQ ID NO:5, SEQ ID NO:6, SEQ ID NO:7, and a sequence which differs from SEQ ID NO:2, SEQ ID NO:5, SEQ ID NO:6, or SEQ ID NO:7 by one base.

28. The method according to claim 23, wherein said antisense initiator sequence is selected from the group consisting of SEQ ID NO:2, SEQ ID NO:5, SEQ ID NO:6, SEQ ID NO:7, and a sequence which differs from SEQ ID NO:2, SEQ ID NO:5, SEQ ID NO:6, or SEQ ID NO:7 by one base.

29. The method according to claim 24, wherein said antisense initiator sequence is selected from the group consisting of SEQ ID NO:2, SEQ ID NO:5, SEQ ID NO:6, SEQ ID NO:7, and a sequence which differs from SEQ ID NO:2, SEQ ID NO:5, SEQ ID NO:6, or SEQ ID NO:7 by one base.

* * * * *